United States Patent [19]

Brown et al.

[11] Patent Number: 6,046,372
[45] Date of Patent: Apr. 4, 2000

[54] PROCESS FOR PRODUCING LIGHT OLEFINS

[75] Inventors: Stephen Harold Brown, Princeton; Larry A. Green, Mickleton, both of N.J.; Mark Fischer Mathias, Pittsford, N.Y.; David H. Olson, Pennington, N.J.; Robert Adams Ware, Wyndmoor, Pa.; William A. Weber, Marlton, N.J.

[73] Assignee: Mobil Oil Corporation, Fairfax, Va.

[21] Appl. No.: 09/055,486

[22] Filed: Apr. 6, 1998

Related U.S. Application Data

[63] Continuation-in-part of application No. 08/725,277, Oct. 2, 1996, abandoned.

[51] Int. Cl.[7] ..................................................... C07C 1/00
[52] U.S. Cl. ............................................ 585/640; 585/639
[58] Field of Search ...................................... 585/640, 639

[56] References Cited

U.S. PATENT DOCUMENTS

| | | | |
|---|---|---|---|
| 4,025,575 | 5/1977 | Chang et al. | 260/682 |
| 4,079,095 | 3/1978 | Givens et al. | 260/682 |
| 4,499,314 | 2/1985 | Seddon et al. | 585/408 |
| 4,677,242 | 6/1987 | Kaiser | 585/638 |
| 4,752,651 | 6/1988 | Kaiser | 585/640 |
| 5,278,345 | 1/1994 | Janssen et al. | 585/640 |

FOREIGN PATENT DOCUMENTS 123449  10/1984  European Pat. Off. .

*Primary Examiner*—Hien Tran
*Assistant Examiner*—Thuan D. Dang
*Attorney, Agent, or Firm*—Peter W. Roberts; Malcolm D. Keen

[57] ABSTRACT

There is provided a process for converting methanol and/or dimethyl ether to a product containing $C_2$ to $C_4$ olefins which comprises the step of contacting a feed which contains methanol and/or dimethyl ether with a catalyst comprising a porous crystalline material, said contacting step being conducted in the presence of an aromatic compound under conversion conditions including a temperature of 350° C. to 480° C. and a methanol partial pressure in excess of 10 psia (70 kPa), said porous crystalline material having a pore size greater than the critical diameter of the aromatic compound and the aromatic compound being capable of alkylation by the methanol and/or dimethyl ether under said conversion conditions.

10 Claims, 4 Drawing Sheets

PROCESS FOR PRODUCING LIGHT OLEFINS

RELATED APPLICATIONS

This application is a continuation-in-part of our U.S. application Ser. No. 08/725,277 filed Oct. 2, 1996, now abandoned, the entire disclosure of which is expressly incorporated herein by reference.

BACKGROUND TO THE INVENTION

The present invention relates to a process for producing light olefins rich in ethylene from methanol and dimethyl ether.

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, and other, four and five carbon olefins. Side by side with this growth, there has been an increasing demand for alkylate, made by reacting olefins with isobutane, for use as a high octane gasoline component.

Burgeoning demand for olefins, particularly ethylene, propylene and butenes, has of course led to periods of shortage, which has led to substantial price increases in the feedstocks to the commercialized technologies. These feedstocks are largely C2 to C4 paraffins co-produced with natural gas and/or paraffinic straight run naphtha. These feedstocks can be substantially more expensive than methane, making it desirable to provide efficient means for converting methane to olefins.

Conversion of methane to methanol followed by conversion of methanol to light olefins is among the most economic routes to make light olefins from methane. In this respect, it is known that methanol or methyl ether can be catalytically converted to olefin-containing hydrocarbon mixtures by contact under certain conditions with particular types of crystalline zeolite materials. U.S. Pat. Nos. 4,025,575 and 4,038,889 for example, both disclose processes whereby methanol and/or methyl ether can be converted to an olefin-containing product over a Constraint Index 1–12 zeolite catalyst, particularly ZSM-5. ZSM-5, in fact, converts methanol and/or methyl ether to hydrocarbons containing a relatively high concentration of light olefins with prolonged catalyst lifetime before catalyst regeneration becomes necessary.

It has also been reported that other types of zeolite catalysts can be used to convert methanol and/or methyl ether to olefin-containing hydrocarbons products containing even higher proportions of light olefins than previously obtained with ZSM-5. For example, U.S. Pat. No. 4,079,095 to Givens, Plank and Rosinski disclose that zeolites of the erionite-offretite-chabazite type, and especially ZSM-34, can usefully be employed to promote conversion of methanol and/or methyl ether to products comprising a major amount of ethylene and propylene. However, while erionite-offretite-chabazite type catalysts are highly selective to light olefins production, such smaller pore zeolites tend to age rapidly in comparison to ZSM-5 when used for methanol/methyl ether conversion.

U.S. Pat. Nos 4,677,242 and 4,752,651 disclose the conversion of methanol to $C_2$–$C_4$ olefins over various silicoaluminophosphates and "non-zeolitic molecular sieves" (such as metal aluminophosphates) and teach that the addition of diluents, such as aromatic materials, having a kinetic diameter greater than the pore size of the molecular sieve increases the ethylene to propylene ratio in the product.

T. Mole, G. Bett, and D. J. Seddon, *Journal of Catalysis* 84, 435 (1983), disclose that the presence of aromatic compounds can accelerate the zeolite-catalyzed conversion of methanol to hydrocarbons. The article reports ethylene yields of 5–22% when methanol is catalytically converted in the presence of benzene or toluene over ZSM-5 at sub-atmospheric pressure, 279° to 350° C., and 100% methanol conversion.

U.S. Pat. No 4,499,314 discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 patent teaches that the increased conversion resulting from the addition of the promoter allows the use of lower severity conditions, particularly lower temperatures, which increase the yield of lower olefins (column 4, lines 17–22). Thus in Example 1 of the patent the addition of toluene as a promoter reduces the temperature required to achieve full methanol conversion from 295° C. to 288° C. while increasing the ethylene yield from 11 wt % to 18 wt %. In the Examples of the '314 patent the methanol feedstock is diluted with water and nitrogen such that the methanol partial pressure is less than 2 psia.

In spite of the existence of methanol conversion processes utilizing a variety of zeolite catalysts and process conditions, there is a continuing need to develop new procedures suitable to convert an organic charge comprising methanol and/or dimethyl ether selectively to light olefin products and in particular ethylene. An object of the present invention is therefore to address this need.

SUMMARY OF THE INVENTION

The present invention resides in a process for converting methanol and/or dimethyl ether to a product containing $C_2$ to $C_4$ olefins which comprises the step of contacting a feed which contains methanol and/or dimethyl ether with a catalyst comprising a porous crystalline material, said contacting step being conducted in the presence of an aromatic compound under conversion conditions including a temperature of 350° C. to 480° C. and a methanol partial pressure in excess of 10 psia (70 kPa), said porous crystalline material having a pore size greater than the critical diameter of the aromatic compound and the aromatic compound being capable of alkylation by the methanol and/or dimethyl ether under said conversion conditions.

Preferably, the molar ratio of methanol and/or dimethyl ether to aromatic compound is greater than 5:1 and preferably is less than 300:1. More preferably, the molar ratio of methanol and/or dimethyl ether to aromatic compound is from 10:1 to 150:1.

Preferably, the conversion conditions include a temperature of 400° C. to 460° C.

Preferably, the conversion conditions are such that the methanol conversion rate is less than 90% and more preferably less than 80%.

Preferably, the porous crystalline material has a pore size between 5 and 7 Angstrom.

Preferably, the porous crystalline material is an aluminosilicate zeolite and most preferably is ZSM-5.

Preferably, the catalyst has an alpha value less than 10 and more preferably less than 2.

Preferably, the porous crystalline material has a Diffusion Parameter for 2,2-dimethylbutane of about 0.1–20 $\text{sec}^{-1}$ when measured at a temperature of 120° C. and a 2,2-dimethylbutane pressure of 60 torr (8 kPa).

Preferably, the porous crystalline material has a Diffusion Parameter of about 0.2–5 sec$^{-1}$.

Preferably, the catalyst contains coke or an oxide modifier selected from oxides of boron, magnesium, silicon and most preferably phosphorus.

Preferably, the catalyst contains about 0.05 to about 20 wt %, and more preferably about 1 to about 10 wt %, of the coke or the oxide modifier on an elemental basis.

DETAILED DESCRIPTION OF THE INVENTION

Figure 1:
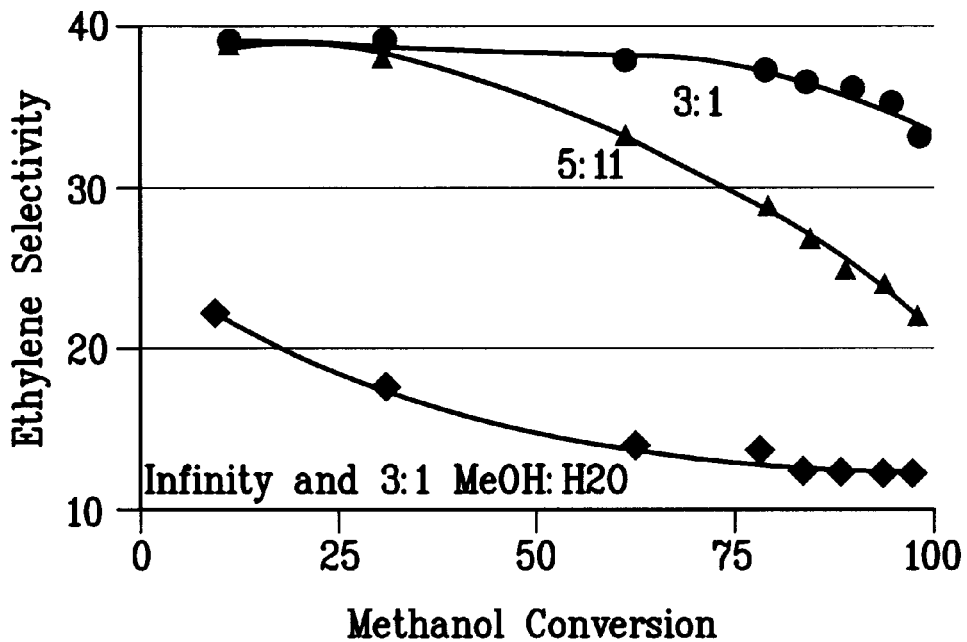
FIG. 1 is a graph plotting ethylene selectivity against methanol conversion for the catalyst of Example 1 when used to convert methanol in the presence of varying amounts of water and toluene.

The present invention provides a process for selectively converting methanol and/or dimethyl ether to $C_2$–$C_4$ olefins, particularly ethylene, over a porous crystalline catalyst and in the presence of an aromatic compound which has a critical diameter less than the pore size of the catalyst and which is capable of alkylation by the methanol and/or dimethyl ether under the conditions of the conversion. The process of the present invention is distinguished from that of U.S. Pat. No. 4,499,314 discussed above in that a substantially water-free methanol feed is contacted with a zeolite catalyst, such as ZSM-5, in the presence of a reactive aromatic compound at a relatively high temperature of 350° C. to 480° C. and a relatively high methanol partial pressure in excess of 10 psia (70 kPa). In addition, the process conditions are preferably controlled so that the methanol conversion is less than 90% and more preferably less than 80%. In this way it is found that ethylene selectivities in excess of 30 wt % can be achieved as compared to the ethylene selectivities of 18–25% by weight reported in the '314 patent.

While not wishing to be bound by any theory of operation, the ethylene selectivity of the process of the invention is believed to follow from our observation that virtually all the ethylene produced via the catalytic partial conversion of methanol to light olefins using zeolite catalysts is derived from the back-cracking of ethyl-aromatic intermediates. The formation of such ethyl-aromatic intermediates is believed to be facilitated in the present process by a mechanism in which the aromatic compound effectively acts as a catalyst in the conversion of two molecules of methanol to one molecule of ethylene. Thus the methylation of aromatics with methanol in zeolites, such as ZSM-5, is a well-known, rapid reaction. The product polymethylbenzenes are stable but are too large to easily exit the pores of the catalyst. Although relatively slow, the next expected reaction of a polymethyl aromatic is skeletal isomerization to a mixed methyl-ethyl aromatic. Once formed, ethyl aromatics are prone to a rapid cracking reaction to form ethylene and the co-catalytic aromatic ring.

Any methanol feed comprising at least 60 wt % of methanol may be used to provide methanol for the use in this invention. Substantially pure methanol, such as industrial grade anhydrous methanol, is eminently suitable. Crude methanol, which usually contains from 12 to 20 wt % water, or even a more dilute solution, may also be used. However, the presence of water as a diluent to reduce the methanol partial pressure is not required. Trace amounts (<1% by weight) of non-aromatic organic impurities, such as higher alcohols, aldehydes, or other oxygenated compounds have little effect on the conversion reaction of this invention and may be present in the methanol feed.

In place of, or in addition to methanol, the non-aromatic reactant feed may comprise dimethyl ether. When this component is present, it can comprise up to 100% of the non-aromatic organic reactant feed or dimethyl ether can be admixed with methanol to form the non-aromatic reactant feed. For purposes of the present invention, it is contemplated to directly convert methanol and/or methyl ether in the feed to a hydrocarbon mixture characterized by a high content of light olefins, especially ethylene. Such amounts of dimethyl ether as may be formed concomitantly in the conversion reaction, however, may be recovered and recycled with fresh organic reactant feed.

The aromatic portion of the feedstock can come from a wide variety of sources. Even substantial amounts of non-aromatic organic components have little impact on the catalytic role of the aromatic co-feed. For this reason, any organic feedstream containing >10wt % aromatics, which have a critical diameter less than the pore size of the catalyst so as to be able to easily diffuse into the catalyst pores, is suitable for use in the process of the invention. These include, but are not limited to, benzene, toluene, xylenes, C9+ reformate streams, light reformates, full-range reformates or any distilled fraction thereof, coker naphtha or any distilled fraction thereof, FCC naphtha or any distilled fraction thereof, and coal derived aromatics. The required aromatic compound can also be produced in-situ by aromatization of the methanol feed. The presence of impurities, such as nitrogen and sulfur compounds, dienes and styrenes, in the aromatic component can be tolerated with little impact when fluid or moving bed embodiments of the invention are employed.

In a preferred embodiment, toluene comprises some or all of the aromatic portion of the feedstock.

The molar ratio of methanol and/or dimethyl ether to aromatic compound will normally be greater than 5:1, since higher concentrations of aromatic compound lead to excessive coking, increased volumes of separation and recycle traffic and minimal gains in total chemical selectivities. Moreover the molar ratio of methanol and/or dimethyl ether to aromatic compound is normally maintained below 300:1, since lower concentrations of aromatic compound lead to little or no noticeable improvement in the ethylene selectivity of the process. However, the amount of aromatic compound required deceases as the pressure increases so that at high pressure it may be possible to achieve a significant improvement in ethylene selectivity with molar ratios of methanol and/or dimethyl ether to aromatic compound above 300:1. Preferably the molar ratio of methanol and/or dimethyl ether to aromatic compound is from 5:1 to 150:1.

The catalyst employed in the process of the invention is a porous crystalline material which has a pore size greater than the critical diameter of the aromatic compound co-feed. Preferred catalysts are porous crystalline materials having a pore size between 5 and 7 Angstrom and in particular intermediate pore size, aluminosilicate zeolites. One common definition for intermediate pore zeolites involves the Constraint Index test which is described in U.S. Pat. No. 4,016,218, which is incorporated herein by reference. In this case, intermediate pore zeolites have a Constraint Index of about 1–12, as measured on the zeolite alone without the introduction of modifiers and prior to any treatment to adjust the diffusivity of the catalyst. In addition to the medium-pore size aluminosilicates, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

In order to increase the concentration of aromatics in the catalyst pores without increasing the aromatic to methanol molar ratio, it may be desirable to use a catalyst having increased diffusional barriers. In particular, it may be desirable to employ a catalyst which comprises a porous crystalline material having a Diffusion Parameter for 2,2-dimethylbutane of about 0.1–20 sec$^{-1}$, preferably 0.1–15 sec$^{-1}$ and most preferably 0.2–5 sec$^{-1}$ when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_{\infty}$, where $Q_{\infty}$ is the equilibrium sorbate loading and is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The intermediate pore zeolites described above as being preferred for the process of the invention may have Diffusion Parameter values in excess of the required 0.1–20 sec$^{-1}$ range. However, the Diffusion Parameter can be controlled or modified to the required value by a variety of methods. For example, the required diffusivity can be achieved by using large crystal forms (greater than 1 micron) of the porous crystalline material, by depositing coke on the material prior to use in the process (as described in U.S Pat. No. 4,097,543) and/or by combining the material with at least one oxide modifier, preferably selected from the group consisting of oxides of boron, magnesium, calcium, silicon, lanthanum and most preferably phosphorus. The total amount of coke or oxide modifier, as measured on an elemental basis, may be between about 0.05 and about 20 wt. %, and preferably is between about 1 and about 10 wt %, based on the weight of the final catalyst.

Alternatively, the required diffusional constraint can be achieved by severely steaming the catalyst so as to effect a controlled reduction in the micropore volume of the catalyst to not less than 50%, and preferably to 50–90%, of that of the unsteamed catalyst. Reduction in micropore volume is derived by measuring the n-hexane adsorption capacity of the catalyst, before and after steaming, at 90° C. and 75 torr n-hexane pressure. Steaming of the porous crystalline material is effected at a temperature of at least about 850° C., preferably about 950 to about 1075° C., and most preferably about 1000 to about 1050° C. for about 10 minutes to about 10 hours, preferably from 30 minutes to 5 hours. To effect the desired controlled reduction in diffusivity and micropore volume, it may be desirable to combine the porous crystalline material, prior to steaming, with a phosphorus modifier. The total amount of phosphorus modifier, which will normally be present in the catalyst in oxide form, as measured on an elemental basis, may be between about 0.05 and about 20 wt. %, and preferably is between about 1 and about 10 wt. %, based on the weight of the final catalyst.

Where the modifier is phosphorus, incorporation of modifier in the catalyst of the invention is conveniently achieved by the methods described in U.S. Pat. Nos. 4,356,338, 5,110,776 and 5,231,064, the entire disclosures of which are incorporated herein by reference. Similar techniques known in the art can be used to incorporate other modifying oxides into the catalyst of the invention.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst employed of the invention preferably has a very low acid activity. Using the alpha test of acid activity disclosed in *Journal of Catalysis*, volume 61, page 395 (1980), the entire disclosure of which is incorporated by reference herein, the catalyst of the invention preferably has an alpha value less than 10, more preferably less than 2.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a relatively high temperature between about 350° C. and 480° C., preferably between about 400 and 460° C., since, as will be illustrated by the following Examples and contrary to the teaching in U.S. Pat. No. 4,499,314, we have found that such a temperature range is critical to the selective production of lower olefins. While not wishing to be bound by any theory of operation, we believe that such a relatively high temperature is essential to the skeletal isomerization and cracking of the polymethylbenzene intermediates produced, whereas higher temperatures lead to excessive coking.

The process of the invention is advantageous in that it is found that the lower olefin selectivity of the product is generally independent of methanol partial pressure so that the necessity in prior art processes to reduce the methanol pressure by the addition of diluents or by operation at reduced pressure can be avoided. The ability to operate at higher methanol partial pressures also allows the absolute yield per pass of olefin product to be increased. A suitable methanol partial pressure for use in the process of the invention is in excess of 10 psia (70 kPa), preferably 15 to 150 psia.

In addition, it is desirable that the conversion conditions are controlled so that the methanol conversion level is less than about 90% and preferably less than 80% since, at higher conversion levels, competing reactions to aromatics methylation, such as olefin alkylation and/or oligomerization to produce $C_5+$ isoolefins and/or olefin conversion to aromatics and paraffins, lower the selectivity to ethylene and propylene. Suitable control of the methanol conversion can, of course, be achieved by variation of the weight hourly space velocity, which typically can vary between about 0.1 and 100, preferably between about 0.1 and 10.

The process of the invention converts methanol and/or dimethyl ether to a light olefin stream in which ethylene comprises over 40 wt %, and typically over 50 wt %, of the $C_2$ to $C_4$ olefins and in which ethylene comprises more than 90 wt %, preferably more than 95 wt %, of the $C_2$ component In addition to the light olefins, a product of the process is xylenes comprising a high proportion of the para isomer, particularly where a diffusionally constrained catalyst is employed as described above.

The invention will now be more particularly described in the following Examples.

In the Examples, micropore volume (n-hexane) measurements were made on a computer controlled (Vista/Fortran) duPont 951 Thermalgravimetric analyzer. Isotherms were measured at 90° C. and adsorption values taken at 75 torr n-hexane. The diffusion measurements were made on a TA Instruments 2950 Thermalgravimetric Analyzer equipped with a Thermal Analysis 2000 controller, a gas switching accessory and an automatic sample changer. Diffusion measurements were made at 120° C. and 60 torr 2,2-dimethylbutane. Data were plotted as uptake versus square root of time. Fixed bed catalytic testing was conducted using a ⅜ (1 cm) outside diameter, down-flow reactor using equipped with a thermocouple. Methanol, water, and aromatics were all pumped to the reactor by way of a vaporizer equipped with a static mixer to thoroughly gassify and mix the feedstocks upstream of the reactor. The reactor was equipped with a backpressure regulator to enable examination of the products at a wide variety of temperature, pressures and WHSV's. The total reactor effluent was analyzed, on line, by gas chromatography. Methanol conversion was calculated based on hydrocarbon formation only. Selectivities to hydrocarbon product were calculated on a "water free" basis.

EXAMPLE 1

Phosphoric acid, kaolin clay, and 450:1 $SiO_2/Al_2O_3$ ZSM-5 were slurried in water and spray dried to make a typical fluid-bed catalyst. The catalyst was calcined in air at 510° C. The finished catalyst contained 40 wt % ZSM-5 and 4.5 wt % phosphorus. This material has an n-hexane sorption of 33.5, a diffusion parameter of 27, and an alpha of about 7. The catalyst was then steamed at 1050° C. for 0.75 hours in 1 atmosphere steam to produce a final catalyst having a Diffusion Parameter of 0.46 $sec^{-1}$ and an n-hexane sorption of 30.6 mg/g.

EXAMPLE 2

A first 0.5 gm sample of the steamed catalyst of Example 1 was used to convert a pure methanol feedstock at 0.5 to 10

WHSV, 430° C., and 1 atm pressure. A wide range of methanol conversions was obtained. The hydrocarbon product ethylene selectivity is plotted vs. methanol conversion in FIG. 1.

A second 0.5 gm sample of the steamed catalyst of Example 1 was used to convert a 3:1 molar methanol: water feedstock at 0.5 to 10 WHSV, 430° C., and 1 atm pressure. A wide range of methanol conversions was obtained. The hydrocarbon product ethylene selectivity is plotted against methanol conversion in FIG. 1.

A third 0.5 gm sample of the steamed catalyst of Example 1 was used to convert a 55:1 molar methanol: toluene feedstock at 0.5 to 5 WHSV, 430° C., and 1 atm pressure. A wide range of methanol conversions was obtained. The hydrocarbon product ethylene selectivity is plotted against methanol conversion in FIG. 1.

A fourth 0.5 gm sample of the steamed catalyst of Example 1 was used to convert a 3:1 molar methanol: toluene feedstock at 0.5 to 5 WHSV, 430° C., and 1 atm pressure. A wide range of methanol conversions was obtained. The hydrocarbon product ethylene selectivity is plotted against methanol conversion in FIG. 1.

FIG. 1 clearly demonstrates that addition of one mole of steam for each 3 moles of methanol to the feedstock leads to a negligible change in ethylene selectivity. In contrast, the addition of toluene in amount as little as 1 mole of toluene for 26 moles of methanol leads to a large improvement in ethylene selectivity, particularly if the methanol conversion is maintained below 90%.

EXAMPLE 3

A further 0.5 gm sample of the steamed catalyst of Example 1 was used to convert a 12:1 molar methanol: toluene feedstock at 1 atm pressure, 0.5 to 5 WHSV and various temperatures between 380 and 480° C. A wide range of methanol conversions was obtained. From this data the ethylene selectivity, toluene conversion, and wt % ethylene/p-xylene at 70% methanol conversion were extracted at each temperature and the results are plotted in FIGS. 2 to 4. The test was then repeated with a feedstock having a 155:1 methanol: toluene molar ratio and again the data is plotted in FIGS. 2 to 4.

Figure 2:
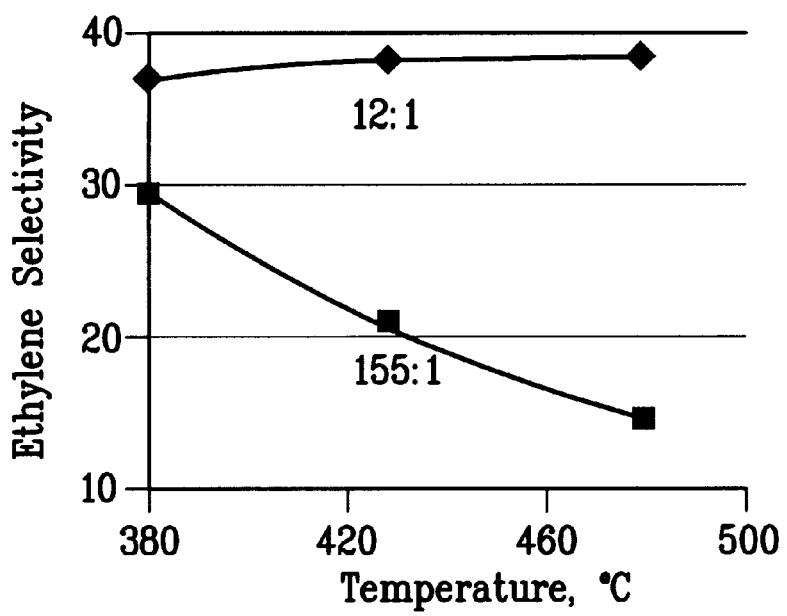
FIG. 2 is a graph comparing the ethylene selectivity with temperature for the catalyst of Example 1 when used to convert methanol in the presence of toluene at methanol to toluene molar ratios of 12:1 and 155:1.
Figure 3:
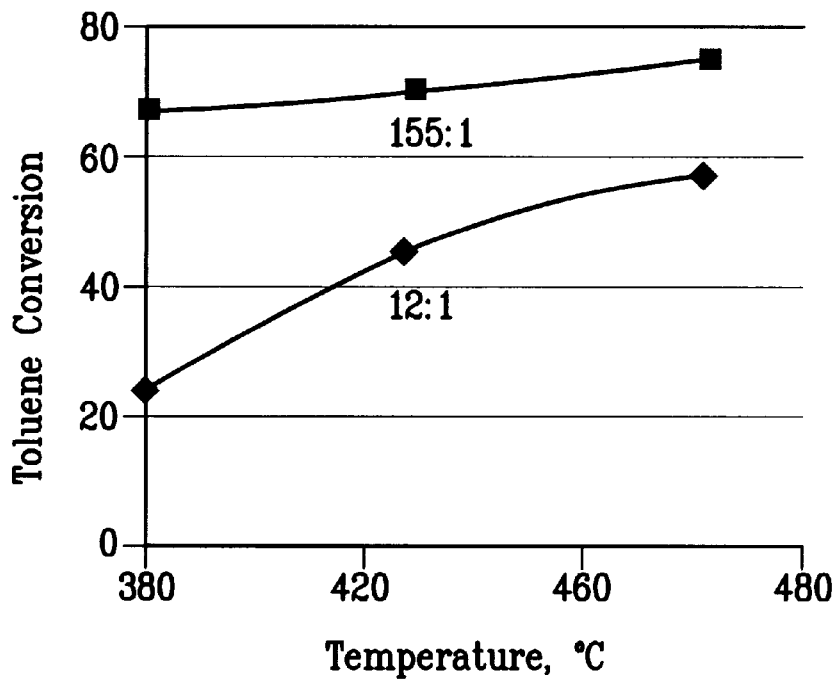
FIGS. 3 and 4 are graphs similar to FIG. 2 but comparing the toluene conversion and wt % ethylene/p-xylene, respectively, with temperature using the same catalyst and methanol to toluene molar ratios.
Figure 4:
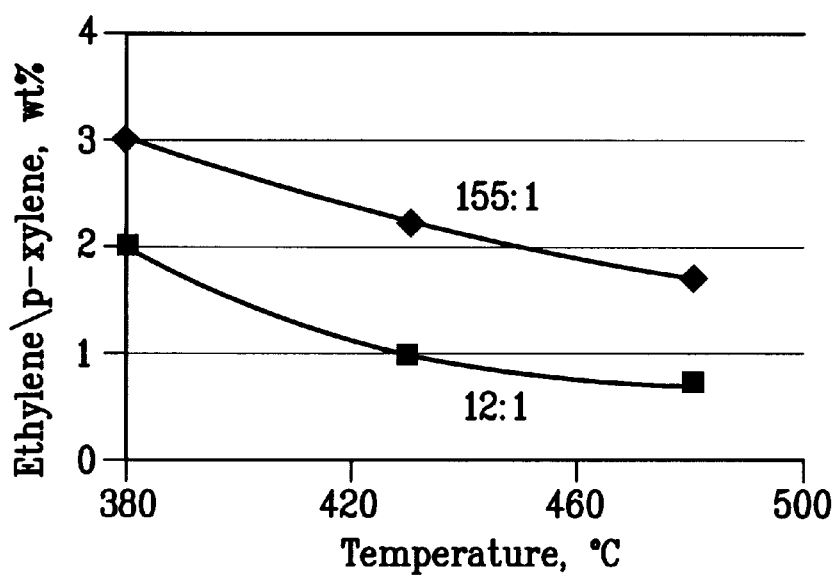

FIGS. 2 to 4 demonstrate that the 155:1 methanol:toluene feedstock does not have enough aromatic cofeed at any temperature to produce as much ethylene as 12:1 methanol-:toluene feedstock. Moreover, as the temperature rises, the ethylene selectivity decreases rapidly with the 155:1 methanol:toluene feed. FIGS. 2 to 4 also show that for the 12:1 methanol:toluene feedstock ethylene selectivity is constant with temperature but the ratio of ethylene:p-xylene in the product decreases rapidly with increasing temperature. Thus control of catalyst, feed, and temperatures enables a producer to choose from among a wide range of product ethylene:p-xylene ratios.

EXAMPLE 4

A sample of the phosphorus-treated, unsteamed catalyst from Example 1 was steamed at 870° C. for 8 hours in 1 atmosphere steam to produce a catalyst having a Diffusion Parameter of 31 sec$^{-1}$ and an n-hexane sorption of 34.9 mg/g. 0.5 gm of this catalyst was used to convert a 26:1 molar methanol: toluene feedstock at 0.5 to 10 WHSV, 430° C., and 1 atm pressure. A wide range of methanol conversions was obtained and ethylene selectivity of the hydrocarbon product is plotted vs. methanol conversion in FIG. 5.

Figure 5:
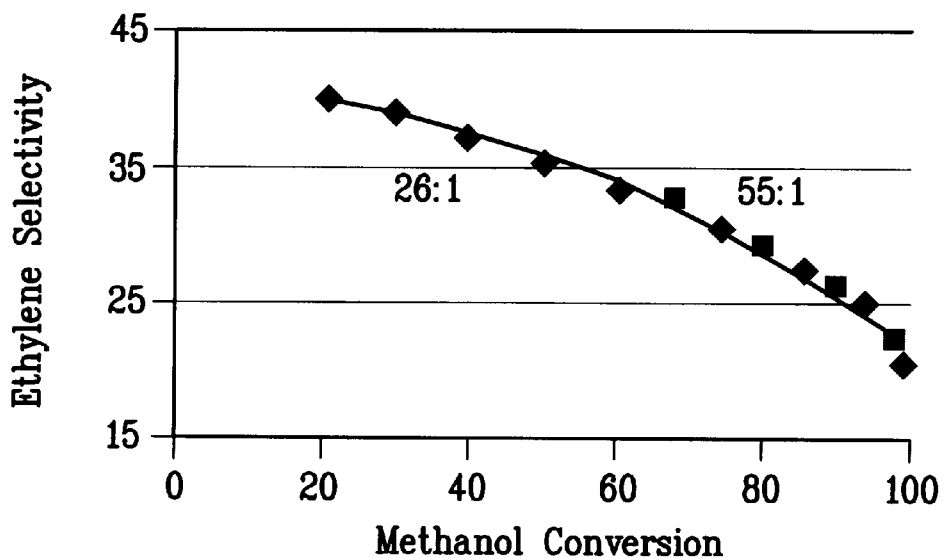
FIG. 5 is a graph comparing ethylene selectivity with methanol conversion for the catalyst of Example 1 at a methanol to toluene molar ratio 55:1 with that for the catalyst of Example 4 at a methanol to toluene molar ratio of 26:1.

By way of comparison, a further sample of the steamed catalyst of Example 1 was used to convert a 55:1 molar methanol: toluene feedstock under the same conditions and again ethylene selectivity is plotted vs. methanol conversion is plotted in FIG. 5.

FIG. 5 demonstrates the relationship between the amount of aromatic co-feed and the diffusivity of the catalyst. The 55:1 feed data with the diffusion restricted catalyst of Example 1 is essentially the same as the 26:1 molar feed data with the less diffusion restricted catalyst of Example 4. This shows that less aromatic co-feed is required to achieve a given product distribution with a more diffusion restricted catalyst than is required with a less diffusion restricted catalyst.

EXAMPLE 5

Figure 6:
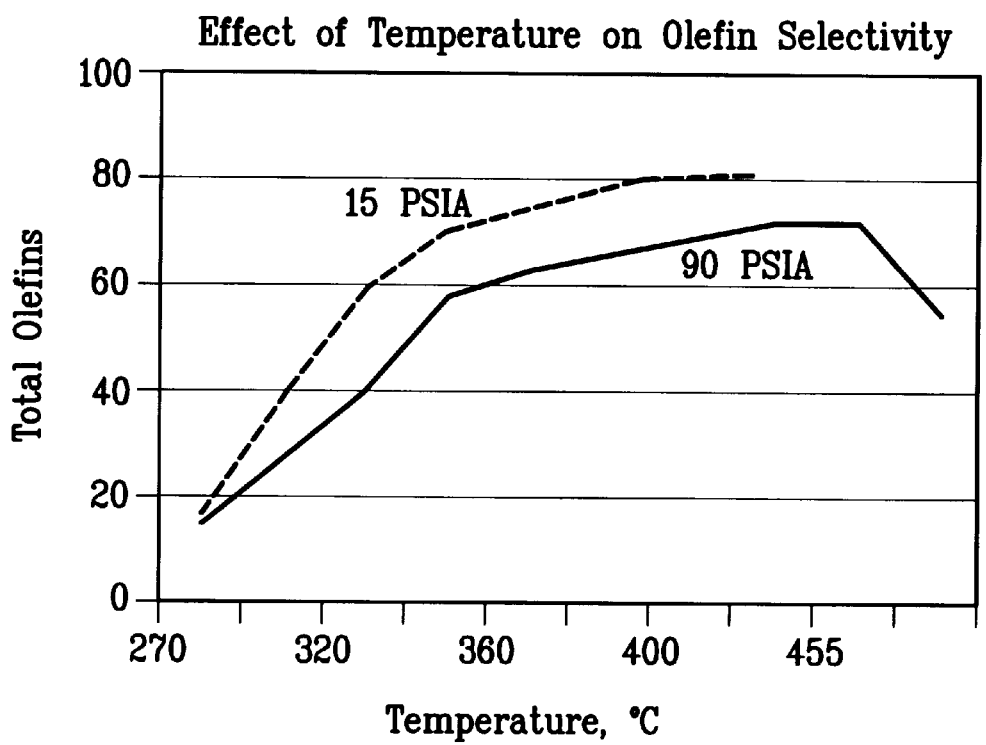
FIG. 6 is a graph comparing olefin selectivity with temperature at methanol partial pressures of 15 and 90 psia for the catalyst of Example 5.

A commercially available FCC additive catalyst, containing 25 wt % ZSM-5 with a silica to alumina molar ratio of 26:1 and 3 wt % phosphorus, was used in this Example. The catalyst had been pre-steamed at 1450° F. (790° C.) for 4 hours and had an alpha value of 3, a Diffusion Parameter of 25 and an n-hexane sorption of 25 mg/g. The catalyst was used to convert a mixture of 90 wt % methanol and 10 wt % toluene (methanol:toluene molar ratio of 26:1) at methanol partial pressures of 15 psia (103 kPa) and 90 psia (620 kPa) and at a methanol conversion level of 80%. Various temperatures between 210 and 490° C. were used and the results are plotted in FIG. 6. From FIG. 6, it will be seen that the conversion of methanol in the presence of toluene is highly selective to olefins at temperatures between 350 and 480° C. and that the olefin selectivity is generally independent of methanol partial pressure especially at temperatures 400 and 450° C.

EXAMPLE 6 (COMPARATIVE)

An alumina-bound ZSM-5 catalyst, containing 65 wt % ZSM-5 with a silica to alumina molar ratio of 26:1, which had been steamed at 515° C. for 1 hour was used in this Example. The catalyst had an alpha value of about 100, a Diffusion Parameter of 1000 and an n-hexane sorption of 77 mg/g. The catalyst was used convert (a) a mixture of 90 wt % methanol and 10 wt % toluene (methanol:toluene molar ratio of 26:1) and (b) pure methanol at a temperature of about 270° C. and a methanol conversion level of about 50% and the results are listed in Table 1. From Table 1 it will be seen that at this low temperature the light olefin yield is marginally less with the toluene co-feed than with the pure methanol feed.

TABLE 1

|  | Run (a) | Run (b) |
| --- | --- | --- |
| Bed Temp, C. | 263 | 262 |
| Furnace T | 260 | 265 |
| WHSV | 0.3 | 0.7 |
| TOS, min | 120 | 63 |
| Feed Comp., wt % |  |  |
| Methanol/DME | 90.000 | 100.000 |
| Toluene | 10.000 | 0.000 |
|  | 100.000 | 100.000 |
| Product Comp., Wt % |  |  |
| Methane | 0.275 | 0.330 |
| Ethylene | 3.167 | 4.170 |
| Ethane | 0.081 | 0.056 |

TABLE 1-continued

|  | Run (a) | Run (b) |
| --- | --- | --- |
| Propylene | 1.929 | 2.483 |
| Propane | 1.362 | 1.730 |
| Methanol/DME | 43.438 | 42.644 |
| Butenes | 1.211 | 1.473 |
| butanes | 1.388 | 1.956 |
| C5–C9 nonA | 4.014 | 5.503 |
| isopentane | 1.504 | 2.309 |
| benzene | 0.000 | 0.000 |
| heptane | 0.000 | 0.000 |
| Toluene | 4.538 | 0.106 |
| EB | 0.023 | 0.029 |
| m + p-xylene | 2.141 | 1.220 |
| o-xylene | 1.823 | 0.159 |
| p-ethyltoluene | 0.313 | 0.334 |
| 1,2,4 TMB | 2.543 | 1.382 |
| C10+ | 3.951 | 1.748 |
| water | 26.300 | 32.369 |
|  | 100.000 | 100.000 |
| Methanol Conversion | 51.7 | 57.4 |
| Methanol to: |  |  |
| Ethylene | 14.2% | 15.5% |
| Propylene | 8.7% | 9.3% |
| Butenes | 5.4% | 5.5% |
| C5–C9 nonA | 24.8% | 29.1% |
| C1–C4 Paraffins | 14.0% | 15.2% |
| Feedstock | 10.9% | 0.0% |
| new rings | 21.9% | 25.4% |
| total olefins | 28.4% | 30.3% |

EXAMPLE 7

Figure 7:
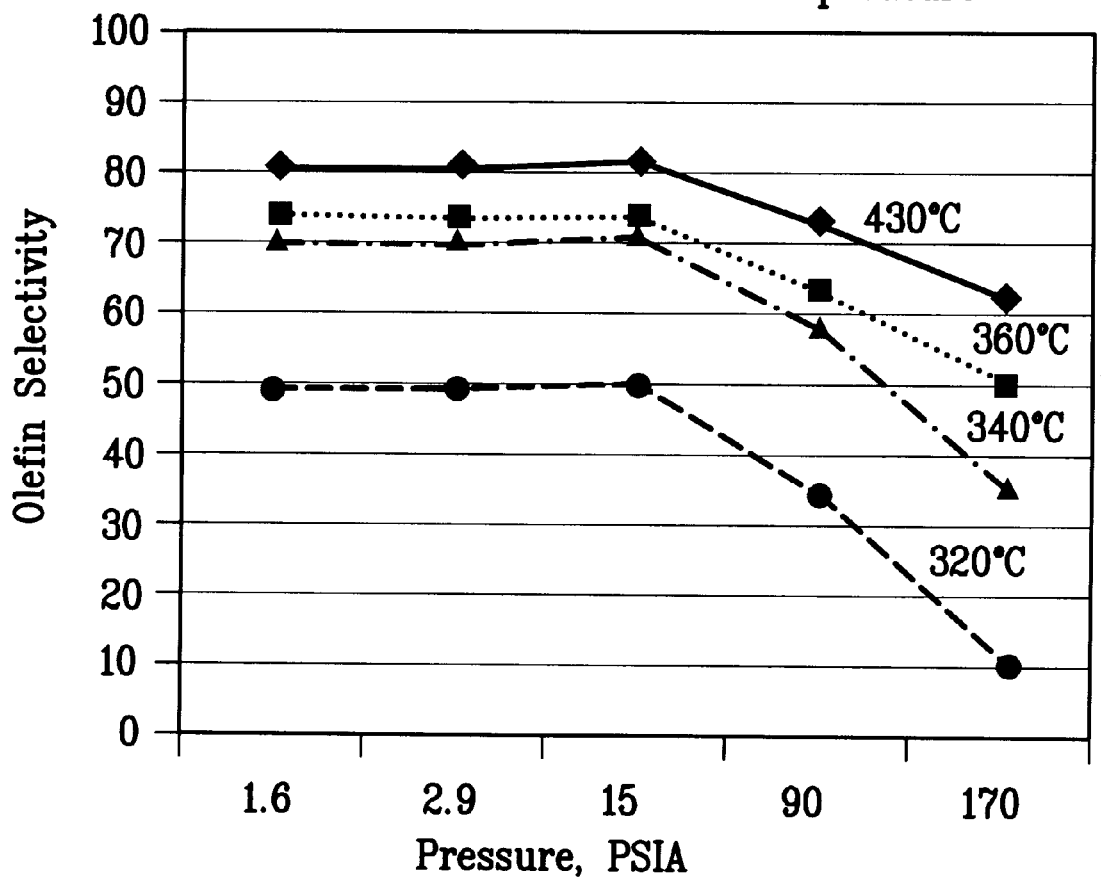
FIG. 7 is a graph comparing the effects of methanol partial pressure on olefin selectivity at different temperatures using the catalyst of Example 5.

The catalyst of Example 5 was used to convert a mixture of 90 wt % methanol and 10 wt % toluene (methanol:toluene molar ratio of 26:1) at various temperatures and pressures. The total olefin selectivity under each condition at a methanol conversion level of about 80% are shown in FIG. 7. The figure clearly shows that at lower temperatures the effect of pressure on total olefin selectivity becomes more and more pronounced. Additionally, these results reemphasize that total olefin selectivity is a strong function of temperature.

What is claimed is:

1. A process for converting methanol and/or dimethyl ether to a product containing $C_2$ to $C_4$ olefins which comprises the step of contacting a feed which contains methanol and/or dimethyl ether with a catalyst comprising a porous crystalline material and having an alpha value less than about 10, said contacting step being conducted in the presence of an aromatic compound under conversion conditions including a temperature of 350° C. to 480° C. and a methanol and/or dimethyl ether partial pressure in excess of 10 psia (70 kPa), said porous crystalline material having a pore size greater than the critical diameter of the aromatic compound and the aromatic compound being capable of alkylation by the methanol and/or dimethyl ether under said conversion conditions.

2. The process of claim 1 wherein the molar ratio of methanol and/or dimethyl ether to aromatic compound is greater than 5:1 and less than 300:1.

3. The process of claim 1 wherein the molar ratio of methanol and/or dimethyl ether to aromatic compound is from 5:1 to 150:1.

4. The process of claim 1 wherein the aromatic compound is selected from the group consisting of benzene, toluene, xylenes, C9+ reformate streams, light reformates, full-range reformates or any distilled fraction thereof, coker naphtha or any distilled fraction thereof, FCC naphtha or any distilled fraction thereof, and coal derived aromatics.

5. The process of claim 1 wherein the conversion conditions include a temperature of 400° C. to 460° C.

6. The process of claim 1 wherein the conversion conditions are such that the and/or dimethyl ether conversion rate is less than 90%.

7. The process of claim 1 wherein the porous crystalline material has a pore size between 5 and 7 Angstrom.

8. The process of claim 1 wherein the porous crystalline material is ZSM-5.

9. The process of claim 1 wherein the porous crystalline material has a Diffusion Parameter for 2,2-dimethylbutane of about $0.1–20 \text{ sec}^{-1}$ when measured at a temperature of 120° C. and a 2,2-dimethylbutane pressure of 60 torr (8 kPa).

10. The process of claim 1 wherein the catalyst has an alpha value less than 10.

* * * * *

UNITED STATES PATENT AND TRADEMARK OFFICE
CERTIFICATE OF CORRECTION

PATENT NO. : 6,046,372
DATED : April 4, 2000
INVENTOR(S) : Stephen Harold Brown, Larry A. Green, Mark Fischer Mathias, David H. Olson, Robert Adams Ware, William A. Weber, Reuel Shinnar It is certified that error appears in the above-identified patent and that said Letters Patent is hereby corrected as shown below:

Column 1,
Line 23, replace "octance" with "octane."

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*